United States Patent
Miao et al.

(10) Patent No.: US 8,270,760 B2
(45) Date of Patent: Sep. 18, 2012

(54) ITERATIVE METHODS FOR DOSE REDUCTION AND IMAGE ENHANCEMENT IN TOMOGRAPHY

(75) Inventors: Jianwei Miao, Los Angeles, CA (US); Benjamin Pooya Fahimian, Beverly Hills, CA (US)

(73) Assignee: The Regents of the University of California, Oakland, CA (US)

( * ) Notice: Subject to any disclaimer, the term of this patent is extended or adjusted under 35 U.S.C. 154(b) by 831 days.

(21) Appl. No.: 12/363,079

(22) Filed: Jan. 30, 2009

(65) Prior Publication Data

US 2009/0232377 A1 Sep. 17, 2009

Related U.S. Application Data

(63) Continuation of application No. PCT/US2007/075220, filed on Aug. 3, 2007.

(60) Provisional application No. 60/835,552, filed on Aug. 3, 2006.

(51) Int. Cl.
*G06K 9/36* (2006.01)
(52) U.S. Cl. ....... 382/280; 382/274; 382/275; 358/3.26; 358/3.27
(58) Field of Classification Search .............. 382/274, 382/275, 280; 358/3.26, 3.27, 463
See application file for complete search history.

(56) References Cited

U.S. PATENT DOCUMENTS

| | | | |
|---|---|---|---|
| 4,506,327 A | 3/1985 | Tam | |
| 4,616,318 A | 10/1986 | Crawford | |
| 4,752,879 A | 6/1988 | Brunnett | |
| 4,888,693 A | 12/1989 | Tam | |
| 5,761,267 A | 6/1998 | Besson | |
| 5,937,102 A | 8/1999 | Jin | |
| 6,304,317 B1 * | 10/2001 | Taniguchi et al. | ............... 355/55 |
| 6,366,638 B1 | 4/2002 | Hsieh | |
| 6,744,848 B2 | 6/2004 | Stanton et al. | |
| 6,862,337 B2 | 3/2005 | Claus et al. | |
| 6,873,744 B2 | 3/2005 | Ottesen | |
| 6,920,240 B2 * | 7/2005 | Rodet et al. | ................... 382/131 |

(Continued)

FOREIGN PATENT DOCUMENTS

JP 2003-260051 A 9/2003

(Continued)

OTHER PUBLICATIONS

Korean Intellectual Property Office (KIPO), International Search Report and Written Opinion dated Sep. 1, 2009, including claims searched, related PCT Application No. PCT/US2009/032733, pp. 1-10.

(Continued)

*Primary Examiner* — Yosef Kassa
(74) *Attorney, Agent, or Firm* — John P. O'Banion

(57) ABSTRACT

A system and method for creating a three dimensional cross sectional image of an object by the reconstruction of its projections that have been iteratively refined through modification in object space and Fourier space is disclosed. The invention provides systems and methods for use with any tomographic imaging system that reconstructs an object from its projections. In one embodiment, the invention presents a method to eliminate interpolations present in conventional tomography. The method has been experimentally shown to provide higher resolution and improved image quality parameters over existing approaches. A primary benefit of the method is radiation dose reduction since the invention can produce an image of a desired quality with a fewer number projections than seen with conventional methods.

55 Claims, 9 Drawing Sheets

U.S. PATENT DOCUMENTS

| | | | |
|---|---|---|---|
| 7,042,217 B2 * | 5/2006 | Zwanenburg et al. | 324/309 |
| 7,076,091 B2 | 7/2006 | Rosenfeld | |
| 7,209,535 B2 | 4/2007 | Chen et al. | |
| 7,315,636 B2 | 1/2008 | Kuduvalli | |
| 7,430,507 B2 * | 9/2008 | Zinser et al. | 704/219 |
| 7,436,507 B2 * | 10/2008 | Moribe | 356/237.4 |
| 7,439,739 B2 * | 10/2008 | Beatty | 324/309 |
| 7,620,440 B2 * | 11/2009 | Elgort et al. | 600/410 |
| 2003/0095596 A1 | 5/2003 | Shimizu | |
| 2003/0169842 A1 | 9/2003 | Nishide et al. | |
| 2003/0198403 A1 | 10/2003 | Ottesen | |
| 2004/0076257 A1 | 4/2004 | McDaniel | |
| 2004/0215072 A1 | 10/2004 | Zhu | |
| 2004/0234022 A1 | 11/2004 | Nukui | |
| 2007/0003122 A1 | 1/2007 | Sirohey et al. | |
| 2007/0053477 A1 | 3/2007 | Ning | |
| 2007/0160304 A1 | 7/2007 | Berkner | |
| 2007/0232890 A1 | 10/2007 | Hirota | |
| 2010/0284596 A1 | 11/2010 | Miao et al. | |
| 2011/0007980 A1 | 1/2011 | Fahimian et al. | |
| 2011/0164799 A1 | 7/2011 | Miao et al. | |

FOREIGN PATENT DOCUMENTS

| | | |
|---|---|---|
| JP | 2004-305331 A | 11/2004 |
| WO | 2007026234 A1 | 3/2007 |
| WO | 2008017076 A2 | 2/2008 |

OTHER PUBLICATIONS

Mao, Yu et al.—"Development and Optimization of Regularized Tomographic Reconstruction Algorithms Using Equally-Sloped Tomography"—IEEE Transactions on Image Processing, vol. 19, No. 5, May 2010, pp. 1259-1268.

Korean Intellectual Property Office (KIPO), International Search Report and Written Opinion dated Dec. 16, 2010, including claims searched, related PCT Application No. PCT/US2012/033162, pp. 1-12.

United States Patent and Trademark Office (USPTO), International Search Report and Written Opinion dated Apr. 10, 2008, including claims searched, related PCT Application No. PCT/US2007/075220, pp. 1-21.

European Patent Office, Extended European Search Report issued on Oct. 31, 2011, related EPO Patent Application No. 07840699.8, counterpart to PCT/US2007/075220, with claims searched, pp. 1-14.

Delaney, A.H. et al.—"A Fast and Accurate Fourier Algorithm for Iterative Parallel-Beam Tomography"—IEEE Trans. on Image Processing, vol. 5, No. 5, May 1996, pp. 740-753.

Ye, J. et al.—"A Self-Referencing Level-Set Method for Image Reconstruction from Sparse Fourier Samples"—Int. Jour. of Computer Vision, vol. 50, No. 3, 2002, pp. 253-270.

Erlandsson, K. et al.—"A New 3D Backprojection and Filtering Method for PET Using All Detected Events"—IEEE Trans. on Nuclear Science, vol. 45, No. 3, Jun. 1998, pp. 1183-1188.

Olson, T.—"Limited Angle Tomography Via Multiresolution Analysis and Oversampling"—Proc. of the IEEE Time Frequency and Time-Scale Analysis, Oct. 4, 1992, pp. 215-218.

Australian Government, IP Australia, Examiner's First Report dated Nov. 30, 2011, related AU Application No. 2007281076, counterpart to PCT/US2007/075220, with claims examined, pp. 1-23.

State Intellectual Property Office of P.R. China, English language translation of the Second Office Action issued Jun. 15, 2011 (pp. 1-7), with claims (pp. 8-16), related patent application No. 200780028681.0, counterpart to PCT/US2007/075220, claiming priority to U.S. Appl. No. 60/835,552, pp. 1-16.

Averbuch, A. et al.—"Fast and accurate Polar Fourier transform"—Appl. Comput. Harmon. Anal. 21, 2006, pp. 145-167.

Miao, J. et al.—"Three-Dimensional GaN-Ga2O3 Core Shell Structure Revealed by X-Ray Diffraction Microscopy"—Physical Review Letters 97, 2006, pp. 215503-1-215503-4.

State Intellectual Property Office of China, The Notification of First Office Action, issued Jun. 9, 2010, Application No. 200780028681.0, including claims examined, 18 pages.

United States Patent and Trademark Office, International Search Report and Written Opinion, PCT International Application No. PCT/US07/75220, issued Apr. 10, 2008, including claims examined, 21 pages.

Japanese Patent Office, Office Action (English translation), counterpart application No. 2009-523075, including claims examined, Jun. 5, 2012, pp. 1-13.

European Patent Office, Communication pursuant to Article 94(3) EPC, counterpart application No. 07 840 699.8, including claims examined, Jun. 18, 2012, pp. 1-10.

Averbuch A. et al., "Accurate and fast discrete polar fourier transform", Conference Record of the 37th Asilomar Conference on Signals, Systems & Computers, Pacific Grove, CA, Nov. 9-12, 2003; [Asilomar Conference on Signals, Systems and Computers], New York, NY: IEEE, US, vol. 2, Nov. 9, 2003, pp. 1933-1937.

\* cited by examiner

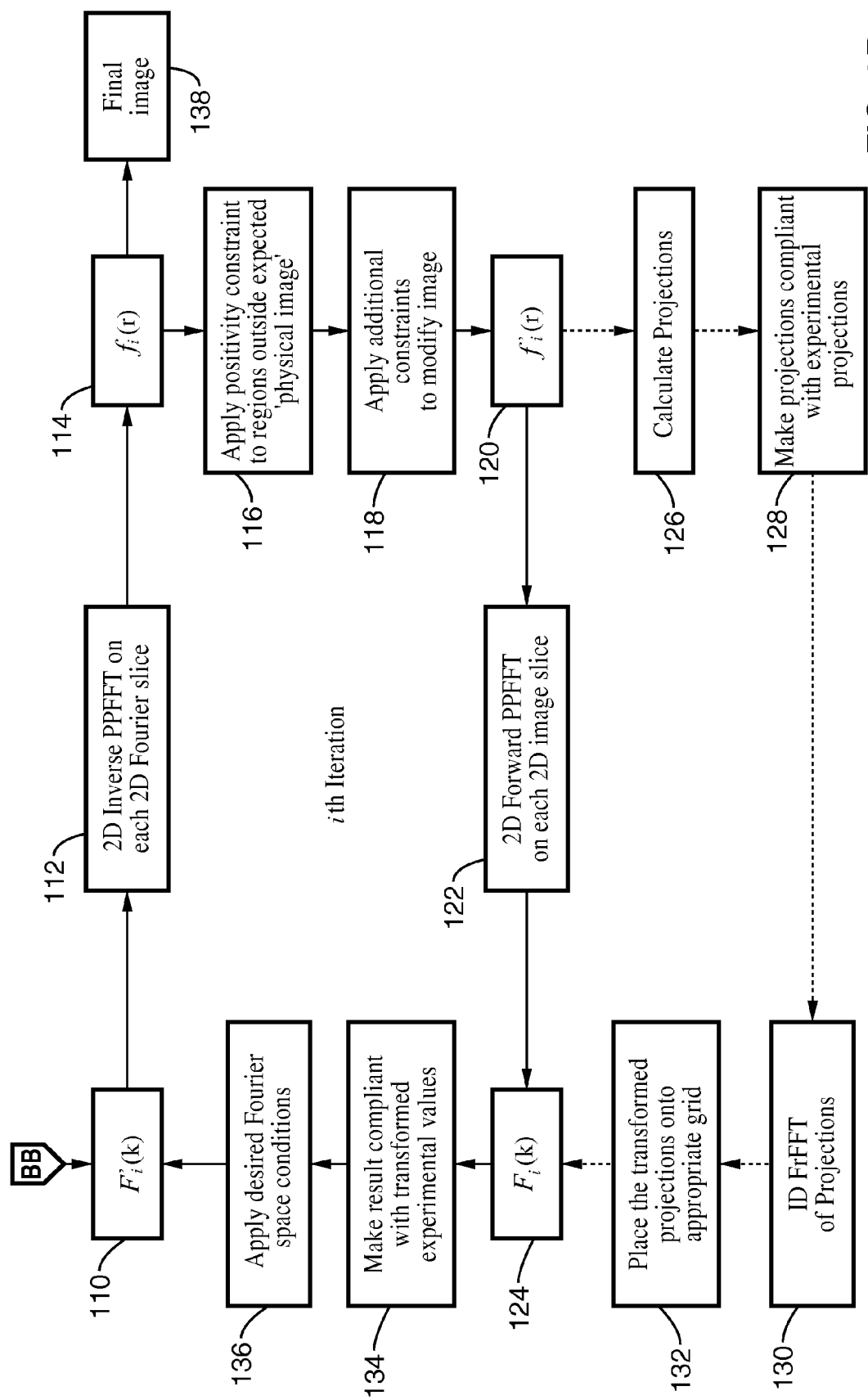

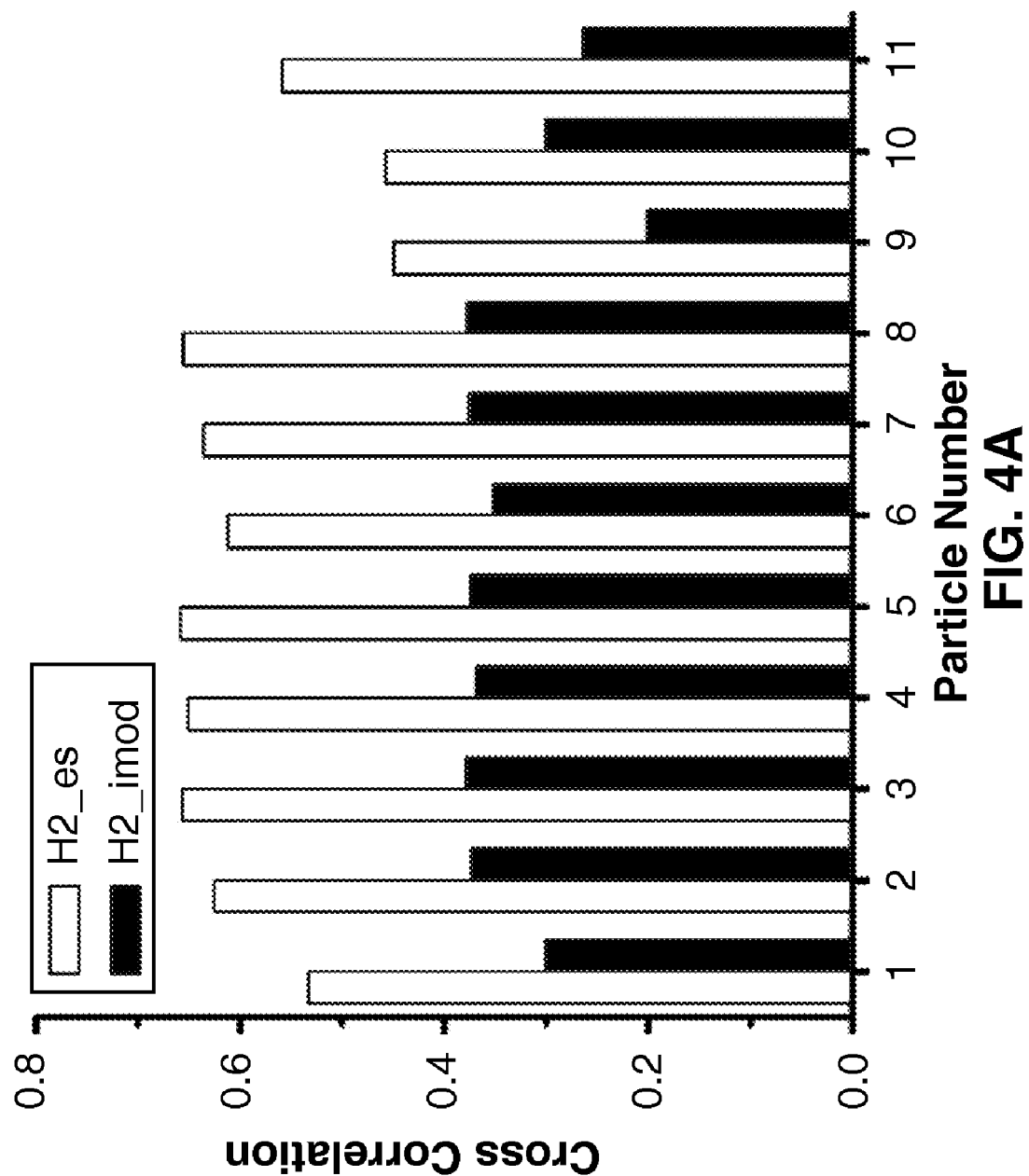

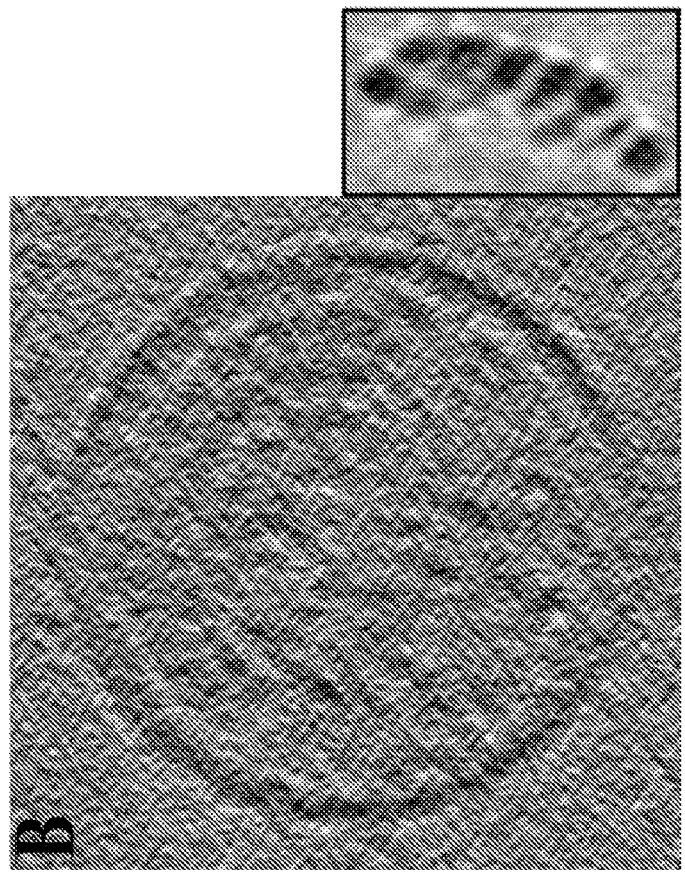
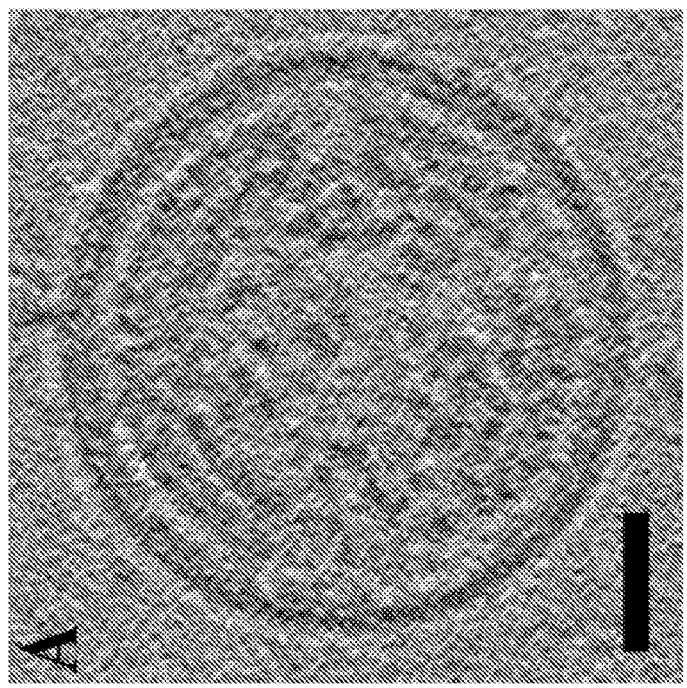
FIG. 5B
FIG. 5A

ITERATIVE METHODS FOR DOSE REDUCTION AND IMAGE ENHANCEMENT IN TOMOGRAPHY

CROSS-REFERENCE TO RELATED APPLICATIONS

This application claims priority from, and is a 35 U.S.C. §111 (a) continuation of, co-pending PCT international application serial number PCT/US2007/075220, filed on Aug. 3, 2007, incorporated herein by reference in its entirety, which claims priority to U.S. application Ser. No. 60/835,552, filed on Aug. 3, 2006, incorporated herein by reference in its entirety.

STATEMENT REGARDING FEDERALLY SPONSORED RESEARCH OR DEVELOPMENT

This invention was made with Government support under Grant Number DE-FG02-06ER46276 awarded by the Department of Energy. The Government has certain rights in this invention.

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to diagnostic and interventional imaging using beams and detectors, and more particularly to systems and methods for creating a three dimensional cross sectional image of an object by the reconstruction of its projections that have been iteratively refined through modification in object space and Fourier space.

2. Description of Related Art

Tomography is an important diagnostic and interventional tool in medicine, biology, geophysics, materials science, archeology, astronomy and the other sciences. It is an imaging technique that produces a cross sectional 2D or 3D image of the internal structures of an object from its projections. The typical tomography apparatus contains a radiation source and a detector that is rotated around an axis extending perpendicularly from the plane of the examination table. Projections of the patient or object are conventionally taken at equal angle intervals such that the angle of the radiating source with respect to the isocenter of the scanner changes by a fixed amount from one projection to the next. Images have been produced from several different beam sources including x-rays, electrons, gamma rays, ions, neutrons, sound waves and others.

A central problem in tomographic imaging is the radiation dose that is directed to the patient or biological specimen as the result of the imaging procedure. With the increasing popularity of medical x-ray CT and fluoroscopic interventional imaging procedures, the long term effects of exposing patients to such ionizing radiation is of increasing concern, especially for pediatric patients. An additional problem in tomographic imaging is the degradation of resolution and other image quality parameters due to the problem of missing or incomplete sets of projection data. Missing projection data can arise from radiation dose restrictions or from practical mechanical limitations in the imaging procedure or imaging system. One example is the missing wedge problem that occurs in electron microscopy, i.e., specimens cannot be tilted beyond $\pm 70°$ and the data in the remaining $\pm 20°$ projections are missing. These difficulties currently limit the resolution of the 3D imaging of cellular and organelle structures.

In addition to the problems of radiation dose and missing projection data, conventional image reconstruction algorithms suffer from inaccuracies from interpolation limitations. Conventional tomography reconstructs a 3D object from a set of equally angled 2D projections. The manner of acquisition inherently forces the projection data into a polar format. Since the set of projections are in polar coordinates and the object is in Cartesian coordinates, interpolation has to be used in the reconstruction process either in object space or Fourier space. Such interpolations may account for a large source of error from the reconstruction algorithm alone and result in a significant degradation of image quality as measured by the resolution, contrast, and signal to noise ratio.

Currently, the most widely used slice reconstruction algorithm is the filtered back projection (FBP). The filtered back projection scheme is computationally fast, but does not offer any solutions for the problem of excessive radiation dose exposure and the problem of image degradation due to missing projection data. In addition, FBP suffers from inaccuracies due to inherent interpolation problems that occur in the back projection process. As a result of the problem of missing projection data and the problem of interpolation, images reconstructed with the FBP method often contain artifacts that degrade the resolution and overall image quality.

In addition to FBP, other reconstruction algorithms exists that are not in general use because they are computationally expensive under practical imaging conditions and also suffer from the problem of interpolation, which reveals itself when the forward projection process is modeled into the system matrix. These methods are also very sensitive to experimental noise and often diverge under realistic noisy experimental situations if the noise is not correctly modeled into the algorithm.

It can be seen that, reconstruction algorithms currently existing in the art, such as Filtered Back Projection, are not mathematically exact and consequently may produce images of lower resolution, contrast, and signal to noise ratio than what may be possible. These introduce inherent errors in the reconstructed image that result primarily from the reconstruction algorithm itself as opposed to experimental error. Furthermore, due to this degradation of image quality, conventional methods of tomography require a high dose of radiation to be administered to a patient to produce suitable images. Consequently, conventional methods have a significantly higher probability of inducing secondary effects such as radiation damage or carcinogenesis to the patient.

There is a need for a system and method for tomographic imaging that limits the exposure of the subject to potentially harmful or destructive radiation that is at the same time accurate, reliable and computationally practical. The present methods satisfy these needs, as well as others, and are generally an improvement over the art.

BRIEF SUMMARY OF THE INVENTION

The present invention provides a system and method for use with any tomographic imaging system that reconstructs an object from its projections. These systems include variants of transmission CT (X-ray Computed Tomography (CT/CAT), X-ray MicroCT, Transmission Electron Microscopy), variants of emission CT (Single Photon Emission CT (SPECT), Positron Emission Tomography (PET)) and their combinations (combined CT/PET, CT/SPECT, SPECT/PET, CT/SPECT/PET systems).

The number of projections that can be acquired in the typical tomographic imaging system is limited by factors such as patient dose, time, and limitations in the scanner design which results in a portion of the projection data that is missing from a scan. The missing projection data can result in decreased resolution and produce artifacts that degrade the image quality of the reconstructed image. The present invention is an iterative reconstruction method capable of solving for a significant portion of the missing projection data. In one embodiment, the invention presents a method to eliminate interpolations present in conventional tomography. The method has been experimentally shown to provide higher resolution and improved image quality parameters over existing approaches. A primary application of the method is dose reduction since the present invention can produce an image of a desired quality with a fewer number projections than conventional methods.

Generally, embodiments of the invention make use of an iterative algorithm that solves for the missing projections and inaccessible data points during the reconstruction process. Once the experimental projection data from the imager is obtained, the projection data is reformulated so that it can be used in accordance of the Fourier Slice Theorem, and optionally, the oversampling method. By applying one of several possible types of Fourier transforms to each projection, a set of Fourier slices in Fourier space can be calculated and placed on an appropriate Fourier space grid in accordance to the Fourier Slice Theorem.

The missing projection data may be filled in by assigning random or preconditioned values to the missing Fourier space data. The missing data is calculated and the image is reconstructed from the Fourier slices by using inverse and forward Fourier transforms to iterate back and forth between object space and Fourier space while modifying the data before each transform. The modifications in Fourier space may include making the resulting Fourier space data of the given iteration consistent with the transformed experimental projection data. The modifications in object space can consist of making the pixel (or voxel) values of the object data provided by the inverse Fourier space conform to a set of user defined values and/or conditions. The cycle of refinement will continue until a termination condition is satisfied and a final image is provided.

Imaging of the raw projections begins by inputting the projection data. If necessary, the projection data is reformulated so that it can be utilized in accordance to the Fourier Slice Theorem. Optionally, the projections may be padded with a suitable number of zeros prior to placement on the Fourier space grid depending on whether oversampling is desired and the degree of oversampling. Padding with zeros will result in the object space data surrounded by mathematical zeros. The knowledge of these zeros can then be used to solve for the missing data in the iterative process.

In accordance to the Fourier Slice Theorem, the projections are Fourier transformed and placed onto a grid in Fourier space. The grid and the Fourier transformation that are used are dependent on one another and may vary. Selection of the grid that the transformed projections are placed upon will influence the selection of a Fourier transform algorithm. The preferred computerized method for performing this step is to use a pseudopolar grid in Fourier space and then perform the Fourier transform (FT) using a Fractional Fast Fourier Transform (FrFFT) algorithm set to match the points of the pseudopolar grid at the given projection angle and slice location. Other computerized implementations of the FT including the non-uniform Fast Fourier Transform (NUFFT) and the conventional Fast Fourier Transform (FFT) can also be used at this stage.

The transformed projections are placed on the appropriate grid at the corresponding location in Fourier space. Placement of the projections on the Fourier space grid can also be accomplished by exact methods such as using the pseudopolar grid in conjunction with the FrFFT, exact or approximate mathematical transformations, or through the Gridding or other interpolation methods.

Once placement on the Fourier space is complete, other optional supplemental transforms can be applied to correlate the slices. Such supplemental transform preferably includes a FT across all slices in the Fourier space.

The locations and values of the Fourier transformed experimental data in Fourier space may also be stored. These values can be used to force the Fourier space data at these locations in future iterations to conform to the experimental data. In one preferred embodiment, the derived Fourier space data at these locations is replaced during each iteration by the transformed experimental values to ensure that the results of the reconstruction are consistent with the experimental data.

The Fourier space data may be modified by assigning values to non-experimental locations and points beyond a resolution circle in Fourier space through preconditioning methods or by the random assignment of values. Preconditioning methods include assigning values to the missing Fourier space data based on the reconstruction of the projection data by some other method. Other modifications may include the enforcement of Fourier space conditions such as symmetry conditions on the phase or amplitude of the Fourier data. If optional supplemental transforms were performed, they may be inverted at this stage with the application of an inverse FFT.

The modified Fourier space data is subject to an inverse Fourier Transform to provide an object space image. For example, this may be done slice by slice with a 2D algorithm or together with a 3D algorithm. The computerized implementation of this step will vary depending on the grid that is used. In a preferred embodiment, the Fourier space is on a pseudopolar grid while the object space is on a Cartesian grid, and the inverse Fourier Transform is an inverse Pseudopolar Fast Fourier Transform (IPPFFT) algorithm. Alternatively, if the Fourier space and object space grids are both Cartesian, a conventional inverse FFT routine may be used.

The object space image that is obtained from the inverse Fourier Transform can be modified to make the object space pixel values conform to previously defined constraints. Constraints are restrictions on the object space image that can be used to aid in solving the reconstructed image. For example, a positivity constraint could require the pixel values in object space to be positive. In a preferred embodiment of the method where a positivity constraint is known to exist for the imaging modality, the pixel values that are negative are modified so that their modified values are closer to zero. This may be achieved by simply setting negative values to zero or pushing the values towards to zero.

Other constraints that may be applied include a requirement that the object space image must be real. Complex values can be transformed to real values by taking the amplitude or real component of the given values. Furthermore, certain designated pixels can be driven towards values that are defined by the user. In addition, pixels in the object space can be modified based on general physical conditions which may restrict the pixel values to some maximum value. Pixels with values above the prescribed maximum values may be modified. In one embodiment, pixels with values that exceed a maximum are mathematically modified so that the modified value is closer to the maximum value than the unmodified value.

If oversampling was used, the physical image region is preferably surrounded by a known number of pixels with values equal to zero. The pixels in this region, referred to as the support, can be used as an additional constraint. Consequently, the object space can be further modified in the support region by pushing the non-zero pixel values in this region towards zero. This method aids the reconstruction by providing additional constraints by which the object space can be modified.

The modified object space data is then subject to a Fourier transformation to provide Fourier space data. In one embodiment, a 2D or a 3D Fourier transformation is applied to the modified object space image. In an alternative embodiment, the Fourier space data is obtained by mathematically calculating the projections from the modified object space image and comparing the mathematically calculated projections with experimental projections. The mathematically calculated projections are also made compliant with the experimental projections. This may be achieved by replacing the points in the mathematically calculated projections at which corresponding experimental projections exist by the experimental projections. An appropriate 1D Fourier Transform is applied to the calculated projections and the transformed projections are then placed onto the appropriate Fourier grid to arrive at the Fourier space data.

The process of mathematically calculating the projections also includes a method by which the object space data is Fourier transformed using the 2D PPFFT algorithm on each slice. The values along the lines of the pseudopolar grid going through the origin of the pseudopolar grid in Fourier space are extracted and then the mathematical projections are calculated using an inverse FrFFT algorithm in accordance with the Fourier Slice Theorem.

The transformed Fourier space data can then be modified to complete the cycle. Optionally, an additional supplemental transform may be applied to the Fourier data. In one embodiment, an error function may be constructed to quantify the difference between the derived Fourier space data with the experimentally measured Fourier data at points where the measured data exist. If the error function reaches its best value as compared to the previous iteration, the Fourier space data corresponding for the iteration is stored. Upon termination of the iterative process, the Fourier space data corresponding to the best error is inverted to provide the best object space image according to the designated error function.

In one implementation, the modification of the Fourier space data includes the replacement of the calculated Fourier slices at the locations of the experimentally measured slices with the stored experimentally measured Fourier slices at points inside the resolution circle. This method ensures that the reconstruction is consistent with the experimental data at each step of the iteration. In another embodiment, the calculated slices are pushed towards the measured slices. In another embodiment, the calculated slices are pushed towards the measured slices only if the calculated slices at a given location differ from the measured slices by a certain threshold percentage. The modification of the Fourier space can also include the application of other Fourier space conditions. Such constraints may include symmetry conditions on the phase and amplitude of the Fourier data. If the initial modification of Fourier space included an additional supplemental transformation, the supplemental transformation can be inverted at this point.

The iterative cycle can begin again with the application of an inverse Fourier transform of the Fourier data to produce slightly refined object space data. The cycle can proceed until a termination condition is satisfied such as a predetermined number of iterations or a monitored error reaches a certain value. A final image can be produced from the results of the refined data.

According to one aspect of the invention, a method is provided that can be adapted to any imaging system that reconstructs an object from its projections and allows projection acquisition from parallel beam and non-parallel beam imagers.

An aspect of the invention is to provide a method that allows a subset of tomographic slices to be reconstructed independently of the other slices and thus permitting parallel computing.

Another aspect of the invention is to provide a method that produces images with improved image quality parameters than found with conventional methods. Such image quality parameters include resolution, contrast, signal to noise ratio and parameters specifying the degradation of an image by artifacts.

Another aspect of the invention is to provide a method for reducing the dose that is imparted to the patient or the imaging object in tomographic imaging systems.

An aspect of the invention is to provide a system and method that can provide detailed two and three dimensional images from a reduced number of projections as well as reduced radiation flux over existing methods to reduce the exposure of the subject to radiation.

Another aspect of the invention is to provide a method for reducing the acquisition time of projection data in tomographic imaging systems. Fast acquisition times are particularly important in imaging an object that moves during the imaging procedures. Such objects may include the organs of a living organism that are in constant motion like the heart and lungs. Motion artifacts in tomographic imaging can be reduced with fast acquisition times.

An aspect of the invention is to provide a method that allows a subset of tomographic slices to be reconstructed independently of the other slices and thus permitting parallel computing.

An aspect of at least one embodiment of the invention includes the acquisition of a partial or full set of equally sloped (or pseudopolar) transmission or emission projections. An equally sloped or pseudopolar projection data set is defined as a transmission or emission projection data set that when converted from the source geometry to the corresponding parallel beam geometry (either exactly or by interpolation), the parallel projections at a given angle lie (within experimental error) along one of the lines of a chosen pseudopolar grid.

According to one embodiment of the invention, a method for reconstructing an object from its projections is provided, comprising the steps of obtaining projection data from an imager; mapping Fourier transformed projection data in Fourier space; converting iteratively the projection data from Fourier space to object space; modifying the projection data in Fourier space and in object space to produce progressively modified projection data, and generating an image from the modified projection data.

According to another aspect of the invention, a computer program product and system is provided comprising a computer-readable storage medium having computer-readable program code portions stored therein and providing for associative relevancy knowledge profiling, the computer program product comprising a first program code configured for obtaining projection data; a second program code configured for mapping Fourier transformed projection data in Fourier space; a third program code configured for converting iteratively the projection data from Fourier space to object space; a fourth program code configured for modifying said projection data in Fourier space and in object space to produce progressively modified projection data; and a fifth program code configured for generating an image from the modified projection data.

Another aspect of at least one embodiment of the invention, a system and method is provided that permits efficient tomographic imaging by 1) converting projection data from source geometry to parallel beam geometry, if necessary. 2) The projections are padded with an appropriate number of zeros to match the oversampling of the pseudopolar grid. 3) The projections at each angle are mapped to their corresponding line on a pseudopolar grid in Fourier space using the Fractional Fast Fourier Transform in accordance to the Fourier Slice Theorem. 4) The values and locations corresponding to the transformed measured experimental data are stored. 5) Optionally, random or preconditioned values can be assigned to the pseudopolar grid points that are missing, unknown, inaccessible or have incomplete projection data. 6) The Inverse Pseudopolar Fast Fourier Transform (IPPFFT) is then applied to the frequency data to obtain an object space image. 7) Constraints are applied to the image in object space. Typically, a positivity constraint requiring the pixel values in object space to be positive is applied by pushing negative values towards zero.

Since the pseudopolar grid is oversampled, the physical object should be surrounded by mathematical zeros in the support region. Consequently, this condition may be used as an additional constraint by pushing non-zero values in the support towards zero. Additionally, if information about pixels in any region is known and or if specific pixels are desired to be driven to desired values, these desired or known values can be used as constraints by pushing the original values to the desired or known values. 8) The forward Pseudopolar Fast Fourier Transform (PPFFT) is applied to the image to obtain the calculated frequency data. 9) An error function may be calculated from the difference of the calculated Fourier space data and the measured transformed experimental data at locations where experimental data exist. The calculated Fourier space data are replaced by the measured transformed experimental projections at locations where the measured data exist to make the reconstruction consistent with the experimental projections. The Fourier space data is further modified by any additional Fourier space constraints. 10) Steps 6 to 9 are repeated a termination condition is satisfied. During step 9 of each iteration, if the error function reaches its lowest (best) value as compared to the previous iteration, the Fourier space data corresponding for the iteration is stored. Upon termination of the iterative process due to the satisfying a termination condition, the Fourier space data corresponding to the best error is inverted by the IPPFFT, and cropped to exclude the support region, to yield the final reconstructed image. The termination condition includes a method by which the iterative algorithm is terminated if the error has not improved by a certain designated percentage in a certain number of iterations. Other termination conditions include satisfying a certain number of iterations or a certain designated error.

Further aspects and objects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

Figure 4D:
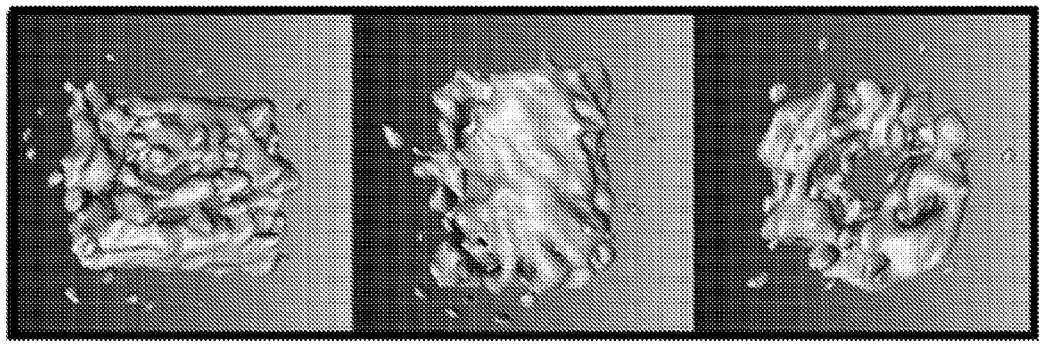
Figure 4C:
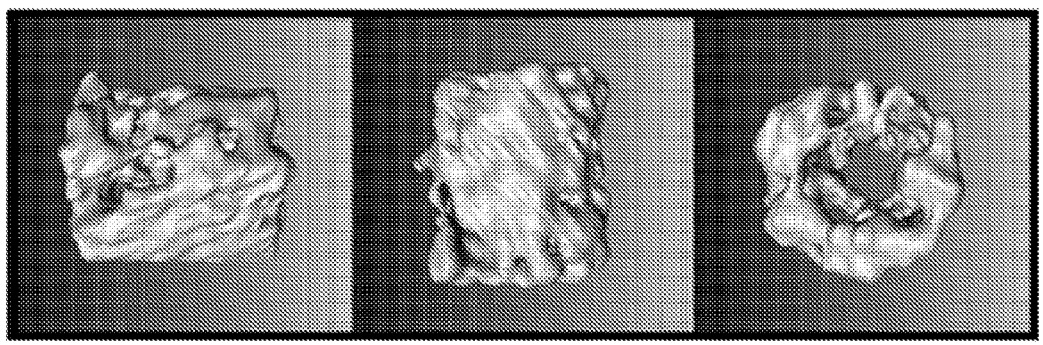
Figure 4B:
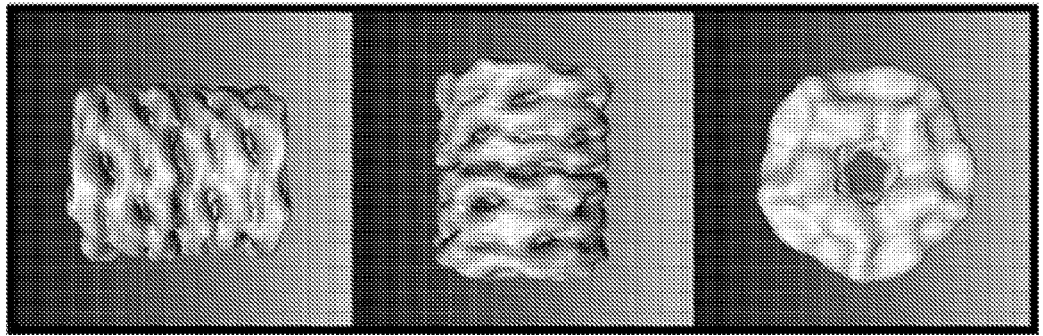

FIG. 4($a$)-4($d$) are cross correlated comparisons of 11 hemocyanin molecules iso-surface renderings imaged by conventional methods and with the methods according to the present invention.

FIG. 5(A)-(D) are 3D image reconstructions of an HIV-1 virus like particle from cryo-EM data imaged by conventional methods and with the methods according to the present invention.

DETAILED DESCRIPTION OF THE INVENTION

Referring more specifically to the drawings, for illustrative purposes the present invention is embodied in the compositions and methods generally shown in FIG. 1 through FIG. 5(D). It will be appreciated that the apparatus may vary as to configuration and as to details of the parts, and that the methods may vary as to the specific steps and sequence, without departing from the basic concepts as disclosed herein.

The present invention provides powerful new techniques for tomographic imaging that produces significantly higher spatial resolution, contrast, and signal to noise ratios than found with conventional methods in Computed Tomography (CT), for example. Problematic interpolations that are inherent in conventional methods of tomography are also eliminated by the invention. Furthermore, the present invention provides a method for significantly reducing the radiation dose that is required to be delivered to the patient or object. Additionally, the invention presents a method for performing high speed imaging by reducing the scan acquisition time.

The method in general can be applied to any imaging system that reconstructs the cross section of an object from its projections. Specific applications to the field of biological and medical diagnostic imaging include the design and operation of common biomedical systems such as X-ray Computed Tomography (CT or CAT), Positron Emission Tomography (PET), Single Photon Emission Tomography (SPECT), Ultrasound, Fluoroscopy, Electron Tomography, and Diffraction Microscopy among others. Although projectional reconstruction is no longer common in Magnetic Resonance Imaging (MRI), it is possible to apply the iterative methods in the present invention to projectional reconstruction of MRI and its variants.

Figure 1:
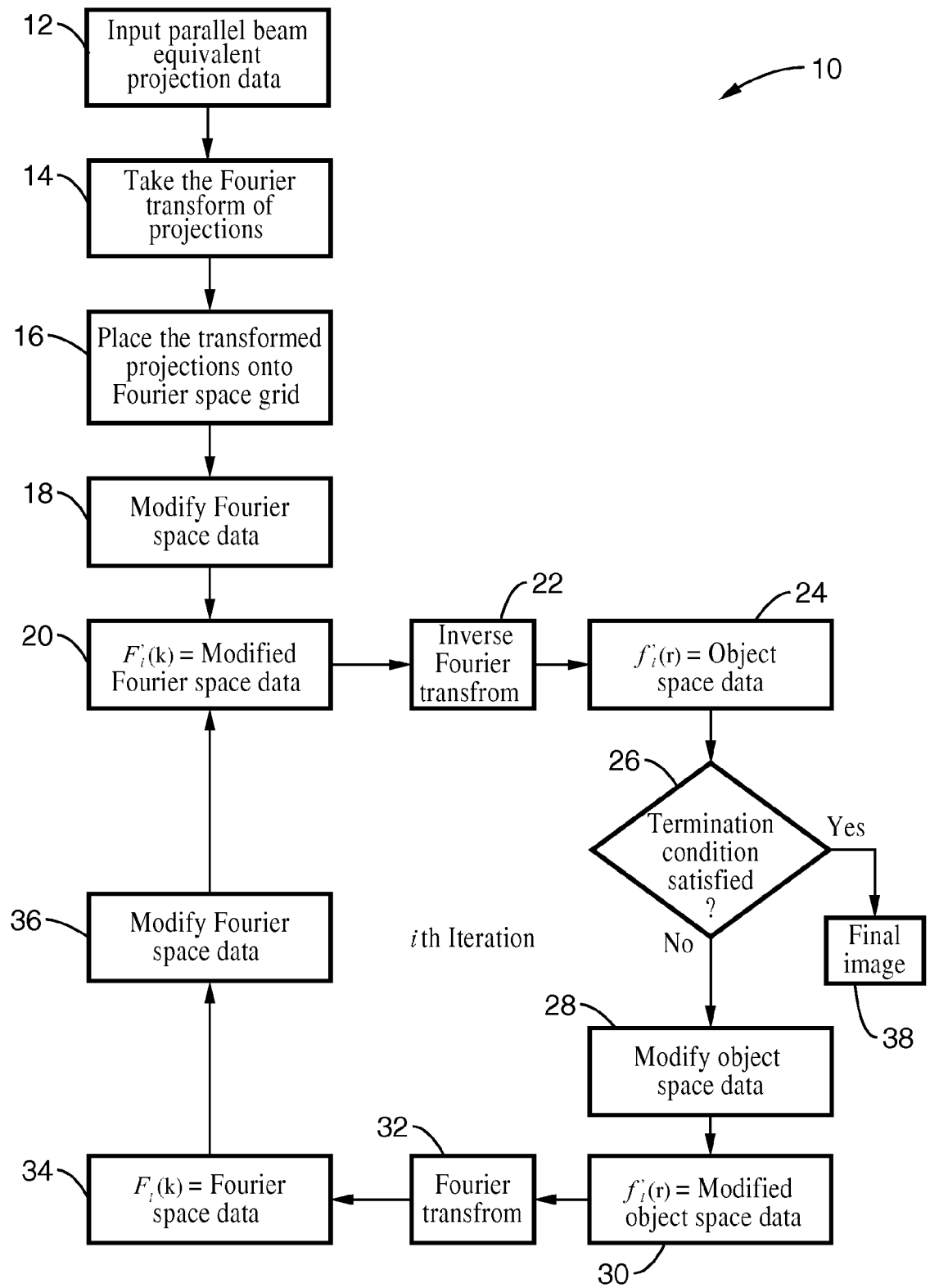
FIG. 1 is a flow diagram of a method for image enhancement and dose reduction in tomography according to one embodiment of the present invention.

Referring now to the flow diagram show in FIG. 1 depicting one embodiment 10 of the invention. In FIG. 1, projection data from a parallel beam system is acquired at block 12. For non-parallel beam systems, projection data can be acquired and then reformulated by a parallel-beam equivalent projection data set. Such reformulation at block 12 can be performed by mathematical transformations in an exact or approximate manner from the system geometry to an equivalent parallel beam geometry. The reformulation can be performed by existing 'rebinning' algorithms present in the art which specifically change the projection data from the given system to a parallel beam equivalent system in an exact or approximate method. Another related method includes an interpolation of the sinogram along the desired parallel projection angular location to arrive at a parallel beam projection.

A further method for converting non-parallel cone or fan beam data to the parallel beam format is provided that comprises a) reconstructing the raw cone or fan beam projection data using standard algorithms for fan/cone beams known in the art, b) operation of a 2D Fourier transform (FT) across all slices, c) extracting the Fourier transformed projections at the desired location from the Fourier data with the use of the Fourier Slice Theorem to arrive at the transformed parallel beam projections, and, d) optionally, if an object space projection data set is desired, operating an inverse 1D Fourier transform to arrive at the parallel beam projection data in object space.

Once the parallel beam data or parallel beam equivalent data has been acquired at block 12, a Fourier Transform of each projection is taken at block 14. The type of Fourier transform that is selected will depend on the type of grid in Fourier space that is desired. 'Fourier space' is defined as a space in which at least one Fourier transformation has been applied to a given data set. The Fourier space can be constructed from other transformations in addition to the Fourier transform. In some situations, the Fourier space used here is similar or equivalent to the phrase 'frequency domain' or 'k-space' in the art. In one embodiment, the Fourier transform of the projections at a plurality of angles and slices at block 14 is a Fractional Fourier Transform set to match points and lines of a pseudopolar grid for each angle in accordance to the Fourier Slice Theorem. Other computerized implementations of the FT such as the non-uniform Fast Fourier Transform (NUFFT) and the conventional Fast Fourier Transform (FFT), can be utilized at this point in accordance with the Fourier Slice Theorem.

The Fourier transforms of the projections are placed on a grid in Fourier space at block 16. For example, a pseudopolar grid has points that sit at the intersections of linearly expanding concentric squares with angularly spaced rays. In contrast to conventional methods of tomography, one embodiment of the present invention acquires the data in such a manner that the projections lay (when converted into parallel geometry) partially or fully along a selected number of equally sloped lines of a pseudopolar grid. The projections at each angle are then exactly mapped to their corresponding lines on the pseudopolar grid in the Fourier space, preferably using the Fractional Fast Fourier Transform (FrFFT). Through this embodiment, interpolations present in conventional methods of tomography can be eliminated.

The placement of transformed projections onto a grid in Fourier space may also be performed with an exact or approximate mathematical transformation, or by interpolating the location and values of a transformed projection on the Fourier space grid. The placement of transformed projections onto a grid in Fourier space may also be performed by the Gridding method. The present invention is not restricted to a specific grid in Fourier space. Other grids that may be used for the Fourier space data include Cartesian type, polar type, 3D polar (i.e., spherical) type, 3D pseudopolar and others.

The Fourier space data of the projections is then modified at block 18 of FIG. 1. Optionally, other supplemental transforms can be applied to at this point as part of the Fourier space modification. For example one supplemental transform includes a Fourier Transform across all slices in the Fourier space to correlate the Fourier space data.

Modifications at block 18 may include filling in missing projection data by assigning values to non-experimental locations in Fourier space. The non-experimental locations can be visualized as regions in Fourier space that the transformed experimental projections do not cover when they are placed on the Fourier space grid. However, the non-experimental regions can be more generally defined as locations which the user or the algorithm designates as non-experimental.

The locations and values of the Fourier transformed experimental data in Fourier space may also be stored. These stored values can be used to force the Fourier space data at these locations in future iterations to conform to the experimental data. For example, in one embodiment, during each iteration, the stored Fourier space experimental data are used to replace the derived Fourier space data at the experimentally available locations to ensure that the results of the reconstruction are consistent with the experimental data.

At this point, the Fourier space data may also be modified by assigning values to non-experimental locations and points beyond a resolution circle in Fourier space through preconditioning methods or the random assignment of values. The resolution circle is a defined circular region in Fourier space which accordingly separates grid points into different regions as defined by being inside, on, or outside the resolution circle.

Preconditioning methods include assigning values to the missing Fourier space data based on the reconstruction of the projection data by any method in the art. The Fourier data and grid may also be modified at this point by extending the grid and padding the Fourier space data with zeros. Other modifications may include the enforcement of Fourier space conditions such as symmetry conditions on the phase or amplitude of the Fourier data. If optional supplemental transforms were performed, they may be inverted at the final stage of this block.

The modified Fourier space data begins an iterative process at block 20 that is able to solve for the missing/incomplete projection data and or experimentally inaccessible data points in Fourier space. These missing projection data typically arise in computed tomography due to the limitations in administered dose or system design or resources in practical applications. Shifting between Fourier space and object space while modifying the data in each space between shifts permits iterative refinements to the data until a final image is reconstructed. The resolution is improved as a result of removing the degradation of image quality that is present due to missing projection data.

At block 22 of FIG. 1, an inverse Fourier transform is performed upon the Fourier space data of block 20 to provide data in the real or object space at block 24. Different types of inverse Fourier transforms may be used at block 20 depending on the Fourier and object space grids that are used. For example, if the Fourier space is on a pseudopolar grid and the object space is on a Cartesian grid, the inverse pseudopolar fast Fourier transform (IPPFFT) may be used. Alternatively, if both grids are Cartesian, a conventional inverse FFT routine may be used. The inverse FT can be performed slice by slice or together at once or on grouped subsets of slices. The slice by slice method may be preferred as it easily allows for parallel computing by distributing subsets of slices across different computers.

At block 26, termination of the process is evaluated to determine if a termination event has occurred. One termination event is the occurrence of a predetermined number of iterations. Another termination event can be the occurrence of a monitored error or image quality parameter function. Yet another termination event can be the occurrence of situation where the error or image quality parameter has not improved in a prescribed number of iterations. In this type of method, the final image may be produced by inverting the Fourier space data corresponding to the best error or image quality parameter, and optionally cropping the object space in accordance to the oversampling used.

Furthermore, the final image does not necessarily have to be based upon the calculated data from the last iteration. In general the final image can be based on the data from previous iterations, or new data that is formed by combining data from previous iterations. For example, the final image can be the average of the object space data from a number of different iterations. In addition, the termination event can be made to occur at any step in the iterative cycle. The final image can be based upon any step of the iterative process.

If a termination condition has not been satisfied at block 26, the object space data at block 24 can be modified at block 28 to provide modified object space data at block 30. Object space data modifications in general make the object space pixel values conform to defined constraints and thereby provide an efficient method to iteratively solve the reconstruction problem in a manner consistent with the constraints. An object space pixel can be made to conform to an expected or desired value (i.e., a constraint) in any mathematical manner. One of the simplest and most common methods for achieving this is by simply replacing the pixel value by a value that is dictated by the constraint. For example, if a constraint dictates that a specific pixel should have the numerical value of zero, the value of the pixel may be changed to zero in the given iteration.

Another method for making a specific pixel conform to a constraint is to modify it so that its value is not exactly the value of the constraint, but after the modification the value of the pixel is potentially closer to the value dictated by the constraint. This method is referred to as 'pushing' the value of a given pixel towards a different value. Mathematically, this method can be achieved in different ways. In one embodiment, the new pixel value can be given by $v'=alpha*v+beta*c$, where $v'$ is the new pixel value, $v$ is the old pixel value, $c$ is the value dictated by the constraint, and alpha and beta are arbitrary adjustable constants. In another embodiment, the mathematical formulation for pushing a pixel value towards another value consists of modifying the given pixel value through the equation $v'=alpha*v+beta*v''+gamma*c$, where $v'$ is the new pixel value, $v$ is the old pixel value, $v''$ is the corresponding pixel value from a previous iteration, $c$ is the value dictated by the constraint, and alpha, beta, and gamma are arbitrary adjustable constants. As a demonstration, assume that the constraint dictates that the value $v$ to be pushed towards $c=0$; as an example, assume that the current value of the pixel is $v=-1$, the value from a previous iteration is $v''=-1.1$, alpha=1, beta=-0.9, and gamma=1 then from the above formula, the new pixel value will be $v'=(1)*(-1)+(-0.9)*(-1.1)+(1)*(0)=-0.01$; hence the pixel value of $-1$ has been pushed towards 0 by being mathematically modified to by $-0.01$.

The modification can take place by a more general mathematical function such as $v'=alpha*v+beta1*v''+beta2*v'''+beta3*v''''+ \ldots +gamma*c$, where beta1, beta2, beta3 . . . are constants and $v'''$, $v''''$ are pixel values from previous iterations. In general, the equation for the modification can be any function of the current iteration pixel value and any number of the previous pixel values. The above modifications can be formulated in many different mathematical ways. However they all constitute the various implementations of the method presented in this invention. In another embodiment, a given pixel value is only changed if it differs from the constraint by a certain percentage threshold.

In one embodiment, a positivity constraint is used to require the pixel values in object space to be positive. According to this constraint, the pixel values that are negative are modified so that their modified values are closer to zero. This may be achieved by simply setting negative values to zero or pushing the values towards to zero. In another embodiment of the positivity constraint, negative values are multiplied by a negative constant to make them a positive number. Other constraints can include conditions dictating that the object space image must be real. Complex values can be transformed to real values by taking the amplitude or real component of the given values.

In an additional embodiment, certain designated pixels can be driven towards defined desired values. In addition, pixels in the object space can be modified based on general physical conditions. For example, a physical constraint may demand the pixel values to be below some maximum value. Pixels with values above the prescribed maximum values can be pushed towards the designated maximum.

Other constraints may include conditions demanding that the object space data change continuously. Other constraints may include conditions on the mathematical derivative of the object space data. A given pixel may be modified so that the mathematical derivative along a certain direction is constrained to some numerical range. In another embodiment, the object space pixels are modified in multiplicative process. As an example, this modification can be given as $v'=alpha(abs(beta*v*v''*v'''*v'''' \ldots ))^{\wedge}(1/n)$, where $v'$ is the new pixel value after modification, $v$ is the pixel value that is to be modified, $v''$, $v'''$, $\ldots$ represent the corresponding pixel values from previous iterations, and n is constant that can be taken to be equal the number of v's appearing in the abs parenthesis, alpha and beta are arbitrary constant, and abs represents the absolute value function. Such a modification is useful for eliminating or de-amplifying variations that are not desired from one iteration to another. As a specific example, if alpha=1=beta, $v=0.5$, $v''=2$, then $v'$ can be given by $v'=1*(abs(1*2*0.5))^{\wedge}(\frac{1}{2})=1$.

If oversampling was used, it is preferred that the physical image region be surrounded by a known number of pixels (as determined by the degree of oversampling) with values equal to zeros. The pixels in this region, referred to as the support, can be used as an additional constraint. Consequently, the object space can be further modified in the support region by pushing the non-zero pixel values in this region towards zero. This method aids the reconstruction by providing additional constraints by which the object space can be modified in that embodiment.

A Fourier transform of the modified object space data at block 30 is applied at block 32 to provide Fourier space data at block 34. This transform converts the modified object space data into Fourier space data that will permit additional or different types of refinements to be made. In one embodiment, the Fourier transform is a 2D Pseudopolar Fast Fourier Transform (PPFFT) applied to each slice. In another embodiment, the Fourier transform is a 3D PPFFT algorithm applied to the totality or individual subsets of the object space data. In another embodiment, the Fourier transform is a conventional 2D FFT applied to each slice. In another embodiment, the Fourier transform is a 3D FFT algorithm applied to the totality or individual subsets of the object space data.

In a further embodiment, projections from the new image at block 30 are calculated and made compliant with the observed experimental projections. Then at block 32, Fourier transforms of the projections are conducted and the projections are placed onto the appropriate Fourier grid in accordance to the Fourier Slice Theorem. This step can also include any additional desired transforms (such as a 1D FT along the slice direction).

The Fourier space data obtained at block 34 can be modified at block 36 to provide modified Fourier space data that has been brought full circle to block 20 of FIG. 1. Optionally, an additional supplemental transform may be applied to the Fourier data at this point if desired.

In one embodiment, an error function may be constructed to quantify the difference between the derived Fourier space data with the experimentally measured Fourier data at points at locations where the measured data exist. For example, an error function can be constructed by calculating the normalized amplitude of the difference between the derived Fourier space data and the experimental Fourier data at the appropriate locations. In one embodiment, if the error function reaches its best value as compared to the previous iteration, the Fourier space data corresponding for the iteration with the best error is stored. Upon termination of the iterative process, the Fourier space data corresponding to the best error is inverted to provide the best object space image according to the designated error function.

In another embodiment, the modification of the Fourier space data includes the replacement of the calculated Fourier slices at the locations of the experimentally measured slices with the stored experimentally measured Fourier slices at points inside a resolution circle. This method ensures that the reconstruction is consistent with the experimental data at each step of the iteration.

In another embodiment, the calculated slices are pushed towards the measured slices. In another embodiment, the calculated slices are pushed towards the measured slices only if the calculated slices at a given location differ from the measured slices by a certain threshold percentage. The modification of the Fourier space includes the application of other Fourier space conditions. These constraints may include symmetry conditions on the phase and amplitude of the Fourier data. If the initial modification of Fourier space included an additional supplemental transformation, the supplemental transformation can be inverted at this point.

The cycle begins again with the application of an inverse Fourier transform at block 22 and continues until a termination condition is satisfied at block 26 and a final image is created at block 38.

It can be seen that there is flexibility in the iterative cycle between object space and Fourier space through the selection of the inverse and forward transforms and the modifications to the object and Fourier space data that take place each cycle. For example, the type of inverse and forward Fourier transforms and grids that are selected can change from cycle to cycle if desired. Likewise, the types of modifications to the object and Fourier space data can be changed from cycle to cycle. This allows for the application of complimentary refinements to take place and missing or incomplete data points to be reliably filled.

Although specific modifications have been disclosed for purposes of illustration, it will be understood that other Fourier and object space modifications and transforms can be used.

Furthermore, the raw projection data can be refined slice by slice independently. Independent slice computation permits parallel computing and greatly reduces the computing demand and the increases speed of image acquisition.

Figure 2A:
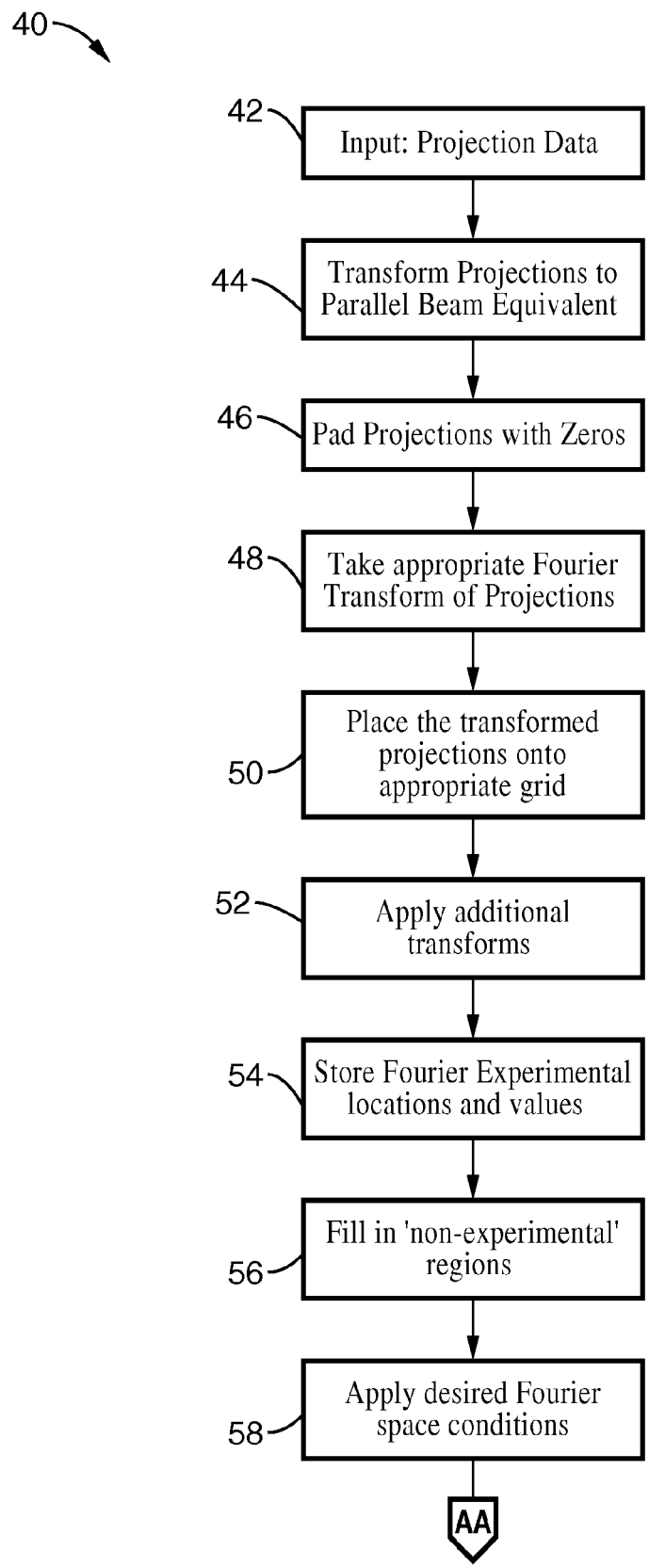
FIG. 2 is a flow diagram of an alternative embodiment of a method for enhanced tomographic imaging and dose reduction according to the invention.
Figure 2B:
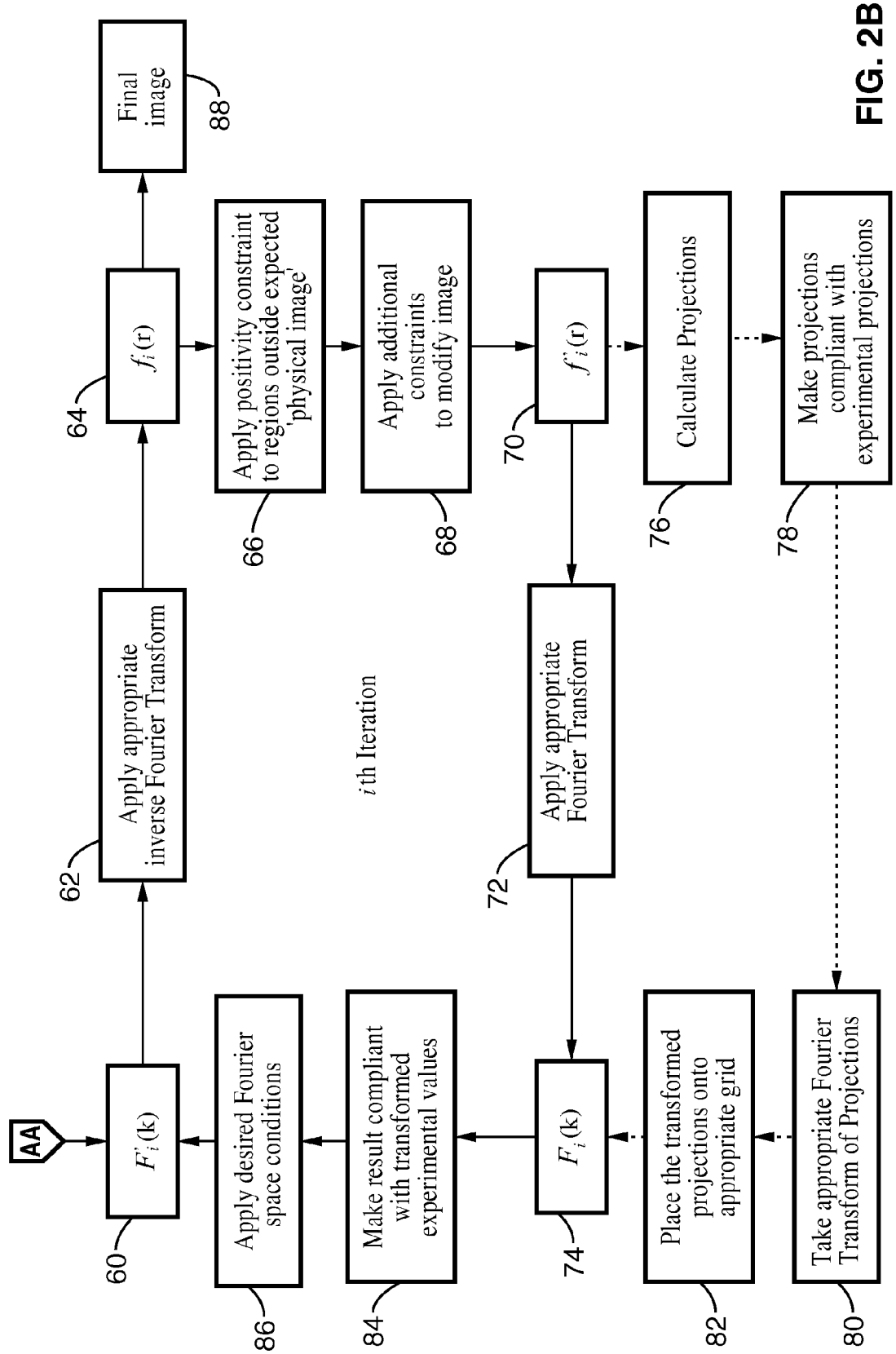

Turning now to FIG. 2, an alternative embodiment 40 of the general iterative reconstruction method is shown. Projections of a patient or object are obtained at block 42 and converted to parallel beam equivalents at block 44, if necessary. The projections are then padded with zeros at block 46 in this embodiment. The Fourier transform of the projections are taken in accordance of the Fourier Slice Theorem at block 48. As indicated previously, the computer implementation of the Fourier transform at this step may be varied in order to optimize or eliminate any interpolations in Fourier space. For example, if the Fourier grid is pseudopolar, many different computer implementations of the Fourier transform, such as the FFT or Fractional FFT (FrFFT), are possible. However, using the FrFFT potentially allows for the elimination of interpolation in Fourier space by varying the parameter of the FrFFT that controls the output spacing in such a manner that the sampling of the output matches the sampling of the pseudopolar grid in a given region.

The transformed projections are placed on an appropriate grid in Fourier space at block 50. Transforms and grids can vary as described previously. At block 52, optional additional transforms can be applied across the data in Fourier space. Such a transform may include applying a Fourier transform across different slices in Fourier space. Optionally, at this stage, the Fourier data can be transformed by extending the grid, and padding the Fourier data by zeros or other desired values.

The transformed Fourier experimental values and locations are stored in block 54. A partial or full subset of the non-experimental region in Fourier space may be filled in at block 56 by methods previously described. At block 58, any desired Fourier space constraints (i.e., conditions) are applied to the Fourier data. The resulting Fourier data from the above is symbolized by $F'_i(k)$, where the subscript i denotes the iteration number. At this step the subscript may be taken to be 0 or 1 depending on the desired convention.

The transformed and modified projections begin an iterative refinement cycle at block 60. The cycle shown in the embodiment of FIG. 2 can take two alternative paths (as shown by the dotted and solid arrows that extend out of block 70) or can produce a result influenced by a combination of both paths. Both cycles begin with the application of an inverse Fourier transform at block 62 of the Fourier data of block 60 to produce transformed data at block 64. Several different transforms 62 are suitable depending on the grids used in Fourier space and object space as previously described.

The transformed data at block 64 may be modified with a positivity constraint at block 66 if desired. If oversampling was used, the physical image region outside of the object should be surrounded by zeros in a region referred to as the support. Pixels in the support can then be pushed towards zero. At Block 68, real or object space any desired conditions (i.e., constraints) may be applied. For example, values may be limited to a certain range.

The modified object space data at block 70, symbolized by $f'_i(r)$ (where i is the iteration number and r symbolizes a vector representing the object space coordinates), can go through to block 74 through different paths, as symbolized by the dotted and solid arrows. In one embodiment, the algorithm only cycles through the steps depicted by the solid arrows. In another embodiment, the algorithm only cycles through the path defined by the dashed lines in order to translate from block 70 to block 74. In another embodiment, depending on the iteration number or prescribed conditions, the algorithm chooses one or the other loop to translate from block 70 to 74. In another embodiment, during a given iteration, the algorithm produces two copies of the data in block 70, and then translates one copy through each path to block 74. At block 74, these copies can be averaged or combined in any desired fashion.

In the path depicted by the solid line, a Fourier transform of the object space data is taken at block 72 as described previously. The computerized algorithms for the Fourier transform can be used depending on the grids used in Fourier and object space.

In the path described by the dashed arrows, the data from block 70 is used to calculate mathematical projections at block 76. Various algorithms in the art that mathematically calculate projections for a given data set, such as common forward projection algorithms, can be utilized. One method to calculate projections mathematically includes the use of the Fourier slice theorem. In this method, Fourier transforms of the object space data across all slices are taken. The transformed projections are extracted according to the Fourier Slice theorem and an inverse Fourier transform is then applied to extracted transformed projection data in accordance to the Fourier Slice Theorem to arrive at the mathematically calculated object space projections.

At block 78, these mathematically derived projections are compared to experimental projections at all or a partial subset of locations. The calculated projections are then made to conform at desired points where experimental projections exist. A point on the mathematically calculated projections can be made to conform to the corresponding experimentally derived point by pushing the value of the mathematically calculated value towards the experimental value. At block 80, a Fourier transform of the projections is applied to the calculated and modified projections of block 78 and placed onto an appropriate grid at block 82, in accordance to the Fourier Slice Theorem, to provide modified Fourier space data at block 74.

Fourier space data at block 74 can come from one of the two cycles individually or can be a combination of the two cycles. Fourier space data of block 74 may be further modified and refined at block 84 by making the results compliant with stored transformed experimental values from block 54 as well as applying desired Fourier conditions at block 86 as previously described. Optionally, at this stage, the Fourier data can be transformed by extending the grid, and padding the Fourier data by zeros or other desired values. The modified Fourier data from block 86 may enter the cycle again at block 60.

The cycle can be terminated at any stage of the iterative cycle to produce a final image. If the cycle is terminated at some point in Fourier space, the Fourier space data can be inverted to provide object space data as a basis for the final outputted image. Before final output, the data to be outputted can be processed in a number of ways. Such processing may include cropping the data, taking the real component of the data, taking the amplitude of data and others.

Figure 3A:
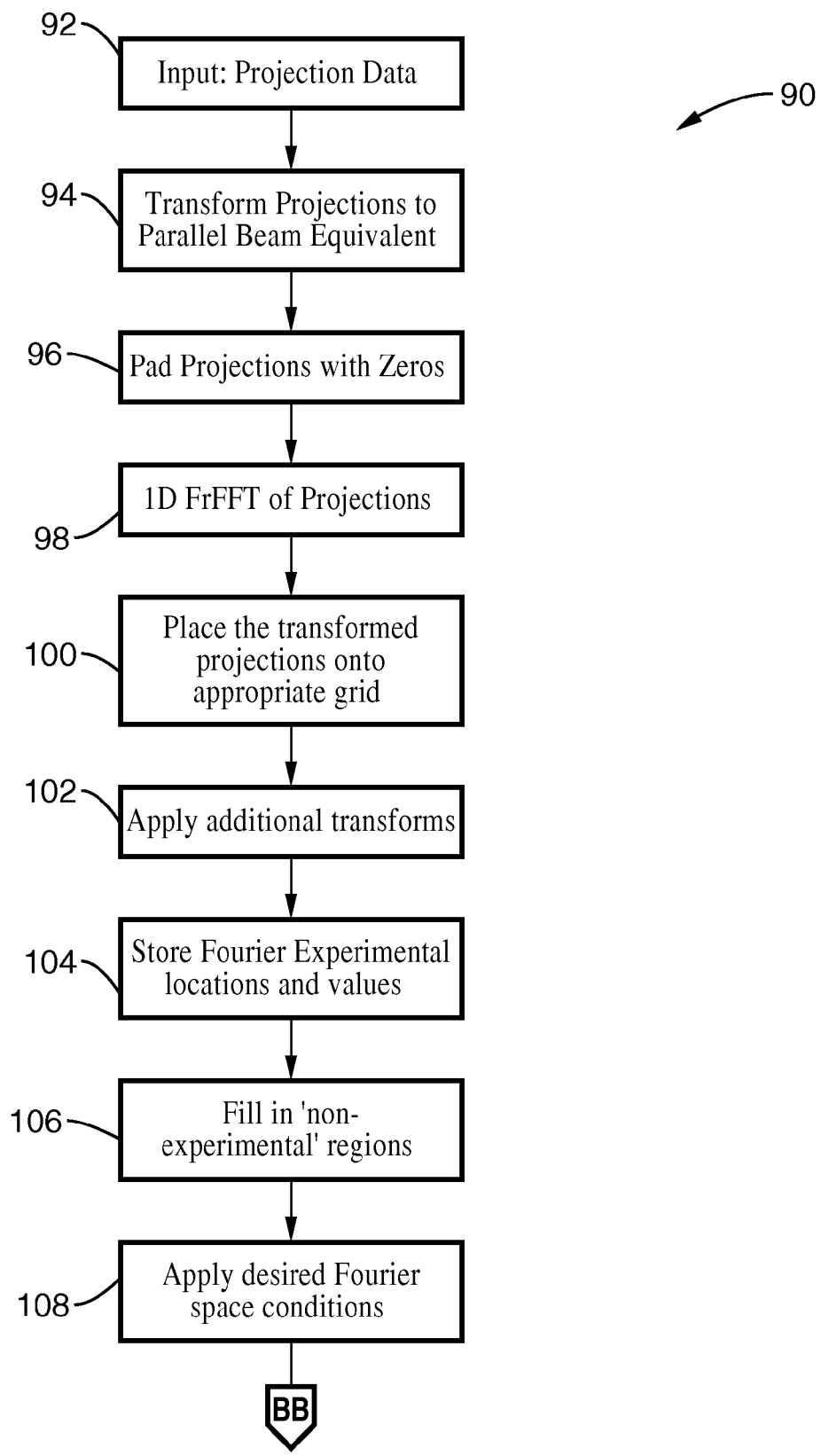
FIG. 3 is a flow diagram illustrating a method of enhanced equally sloped tomographic imaging and dose reduction according to an alternative embodiment of the present invention.

Turning now to FIG. 3, an alternative embodiment 90 of the invention is shown that is particularly preferred for use with a partial or full set of equally sloped transmission or emission parallel equivalent projections that lie (within experimental error) along one of the lines of a chosen pseudopolar grid.

Generally, this embodiment uses a 1D FrFFT transform in a manner consistent with the Fourier Slice Theorem and with the output sampling matching the grid sampling of the Fourier space grid at the given slice location and projection angle. A pseudopolar type grid in Fourier space is used that is preferably oversampled by a factor of two relative to the object space grid. The Fourier space grid specifically consists of a 2D pseudopolar grid at each slice location and uses a Cartesian grid in object space.

Transformation from Fourier space to object space and back is accomplished with 2D Inverse and Forward Pseudopolar Fast Fourier Transform (IPPFFT) algorithm across all slices of the Fourier space. In one embodiment, no additional supplemental transformations are applied, and the reconstruction is performed slice by slice in a parallel computing environment.

Projection data is obtained at block 92 of FIG. 3. In one embodiment, the imaged subject, detectors, and/or the radiation source are rotated in manner that the majority of the resulting reformulated projection data, within experimental error, lies along isocentric lines formed by grid points of a grid in Fourier space. An isocentric line is a line intersecting a reasonable number of grid points as well as intersecting a central point of a slice or set of slices of a grid. Examples of such lines include the lines formed on 2D or 3D pseudopolar grids that intersect a central point in each slice of the grid or intersect the central point of a set of slices. Other grids include polar and spherical grids. Since the angle of a given line with respect to the isocenter of the grid in Fourier space is equivalent to the angle in object space, the angles of the lines of the pseudopolar grid can be used to determine the angles of the possible equally or pseudopolar lines in object space.

One illustrative embodiment of the method includes rotating the sample in a transmission CT modality, such as the Transmission Electron Microscope, a SPECT or PET system or a medical x-ray CT/CAT scanner, in such a manner that resulting projections are parallel within experimental error to a partial set of lines defined by the Fourier space grid. If the preferred pseudopolar grid is used, the projections will reside along a partial set of pseudopolar lines. Since SPECT systems can be considered as parallel beam systems, the detectors as defined by the Gamma Camera or head(s) of the scanner can be rotated in such a manner that angles the head(s) make with the isocenter of the scanner correspond, within experimental error, to a partial set of angles made by the lines of pseudopolar grid that intersect the center of the grid. For PET systems, the detector elements can be arranged in such a way that a majority of the resulting reformulated projections are approximately parallel to a partial set of lines defined by the Fourier space grid. In the case of the pseudopolar grid, this can be achieved by arranging the detector elements along a square at each slice location as opposed to the conventional circular design.

The projections that are acquired at block 92 and block 94 are optionally padded with zeros at block 96. In the embodiment shown, a 1D Fractional Fast Fourier Transform (FrFFT) is applied to the acquired projections at block 98. The parameter that controls the output spacing of the FrFFT should be set to match the spacing of the points of the lines of the Pseudopolar grid for the specific angle.

The values of the transformed projections from block 98 are placed onto a pseudopolar grid at block 100. Optionally, additional transforms such as a 1D Fourier Transform along different slices may also be applied at block 102. The transformed Fourier experimental locations and values for each projection may be stored at 104 in the embodiment shown.

At block 106, values of non-experimental locations in Fourier space may be assigned and any Fourier space constrains may be applied at block 108 to produce the starting Fourier space data at block 110.

At Block 112, a 2D Inverse Pseudopolar Fast Fourier Transform is performed on each two dimensional Fourier slice from the data obtained at block 110 to provide an object space image at block 114.

Positivity constraints are applied to the support at block 116 and other constraints at block 118 to provide modified object space data at block 120.

The modified object space data can be manipulated and can be translated to block 124 through alternative paths symbolized by the solid and dotted arrows or through a combination of paths as previously discussed in this document. A 2D forward Pseudopolar Fast Fourier Transform is applied to each slice of the image at block 122 in the embodiment shown in FIG. 3 to produce modified Fourier space data 124.

Alternatively, or in combination with the solid arrow path, projections can be calculated from the object space data from block 120 at block 126. The calculated projections are made to be compliant with experimental projections at block 128 as previously discussed. A 1D FrFFT is then performed on the calculated projections using the appropriate output spacing parameter for a pseudopolar grid at block 130 and placed on to a pseudopolar grid at block 132. The modified Fourier space data at block 124 may be made compliant with transformed experimental values at block 134 and Fourier space conditions may be applied at block 136. The modified Fourier space data then enters the cycle again at block 110. The iterative cycle of transforms and modifications continues until a termination condition is met. A final image is then generated at block 138.

In conjunction with an equally sloped acquisition, this embodiment of the method resolves the interpolation problem typically found in conventional methods of tomography by matching the projections to isocentric lines of the pseudopolar grid and by matching the sampling of the FrFFT to that of the pseudopolar grid for each projection. As a result, it is possible to eliminate the degradation of resolution and other image quality parameters that typically exist in tomographic reconstructions due to the interpolation problem. Furthermore, through the use of the iterative algorithm, the missing data can be solved and the process of solving for the missing data can be confirmed in computer simulations. Simulations generally show that after each iteration prior to the termination condition, there is a correlation between the reconstructed image with that of an ideal or perfect reconstruction that does not have a missing data increase. Besides providing a method for higher quality tomographic reconstruction, the invention provides methods for dose reduction and high speed imaging through the reduction of the number of required projections and/or radiation flux.

Embodiments of the present invention are described with reference to flowchart illustrations of methods and systems according to embodiments of the invention. These methods and systems can also be implemented as computer program products. In this regard, each block or step of a flowchart, and combinations of blocks (and/or steps) in a flowchart, can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts support combinations of means for performing the specified functions, combinations of steps for performing the specified functions, and computer program instructions, such as embodied in computer-readable program code logic means, for performing the specified functions. It will also be understood that each block of the flowchart illustrations, and combinations of blocks in the flowchart illustrations, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s).

The invention may be better understood with reference to the accompanying examples, which are intended for purposes of illustration only and should not be construed as in any sense limiting the scope of the present invention as defined in the claims appended hereto.

EXAMPLE 1

In order to demonstrate the functionality of the invention, the pseudopolar embodiment of the invention was applied to a 3D image experimental reconstruction of hemocyanin molecules. The hemocyanin molecule consists of a double-layered and hollow barrel complex about 30 nm in diameter and 35 nm in length. A data set was acquired by tilting the specimen from −69.4° to +69.4° with a total of 105 projections. Image reconstruction was carried out using the said method and the conventional method of FBP. The projection data from the imager was padded with zeros, Fourier transformed, placed onto a pseudopolar grid, and translated through the iterative process as described by the solid arrow loop of the diagram of FIG. 3. A positivity constraint was used in object space. In Fourier space, the data was updated and was made to conform to the experimental data. To perform a quantitative comparison, 11 individual hemocyanin molecules of the two reconstructions were chosen. The particles were compared with a model averaged from hundreds of hemocyanin molecules. FIG. 4(*a*) shows the cross-correlation values between the reconstructed particles and the model, which indicates that the said method improves the cross correlation values by about 40%. The iso-surface renderings shown in FIG. 4(*b*)

through FIG. 4(d) further demonstrated that the said method is superior to the conventional reconstruction shown in FIG. 4(d).

EXAMPLE 2

To demonstrate the adaptability of the methods of the invention, images of HIV-1 virus-like particles (VLPs) were reconstructed. The subject particles were plunge-frozen onto EM grids and imaged in a 300 kV FEG TEM. The tilt angles ranged from −70° to +70° with a fixed angular increment of 1°. The 3D structure of a HIV-1 VLP was reconstructed by using conventional methods for purposes of comparison with images produced by the present invention. Referring now to FIG. 5A through FIG. 5D, image reconstruction of the HIV-1 like particle from cryo-EM data is shown. FIG. 6 (A) and FIG. 6(B) show sectioned images in the XY and YZ plane with 15-slice averaging and no denoising. The inset shows some of the gold fiducial markers reconstructed by conventional methods.

The same data set was reconstructed by the pseudopolar embodiment of the present invention. Since the tilt series has a fixed angular increment, it was possible to calculate each equally sloped tilt from the neighboring equally angled ones. According to the simulations, this approximation method only slightly affected the precision.

Figure 5D:
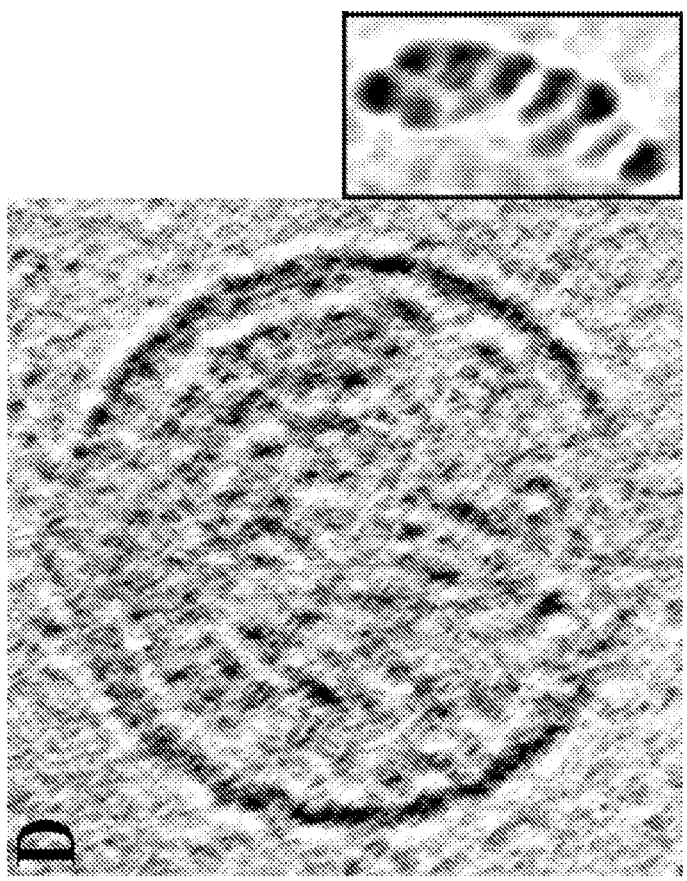
Figure 5C:
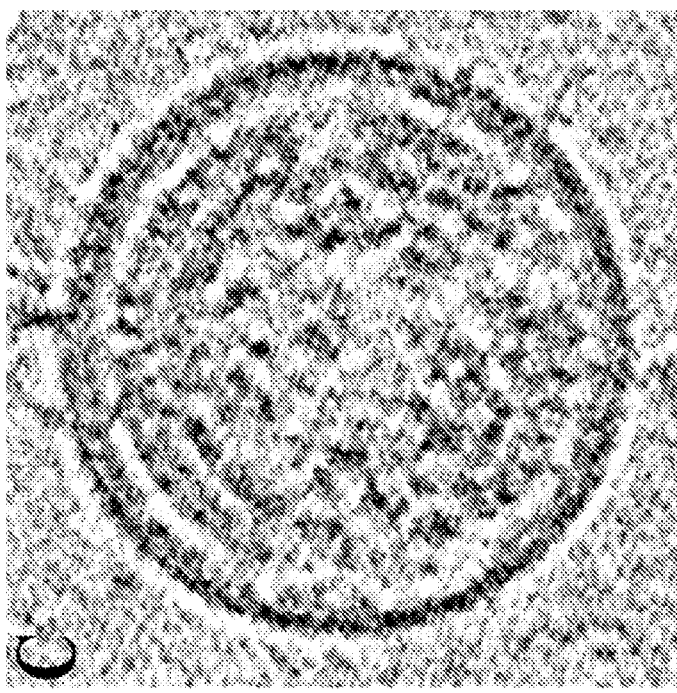

As seen in FIG. 5(C) and FIG. 5(D), images were obtained from use of the method in the XY and YZ plane with 15-slice averaging and no denoising. The inset shows the same gold fiducial markers reconstructed by the method. The reconstruction comprised reformulating the projections and padding them with zeros. Thereafter a FrFFT was applied to the reformulated projections and the transformed projections were placed on a pseudopolar grid. The data was translated through the iterative process as depicted in the solid line loop of FIG. 3 and the reconstruction was terminated after 100 iterations and a final image was produced. The images from the application of the method in FIG. 5(A) and (B) show a better contrast and look sharper than the conventional images and potentially new detail can be seen in the reconstruction.

The invention has been shown experimentally to yield higher resolution images than produced by conventional reconstruction methods such as Filtered Back Projection (FBP). In addition, the images produced by the invention have been shown to have improved image quality parameters such as contrast and signal to noise ratio when compared to conventional FBP reconstruction.

In addition to image enhancement, one of the most important benefits of the invention is the reduction in exposure to radiation in tomographic imaging. It is possible to lower the radiation dose to the patient or object through either lowering the flux of radiation or by decreasing the number projections taken in transmission CT scans due to the increased accuracy of reconstructions and image quality parameters such as resolution, contrast, and signal to noise ratio provided by the present invention. For example, with transmission CT, the flux can be simply lowered by altering the current to the source (for example the mAs of an X-ray tube). Furthermore, a lower number of projections can be acquired in transmission CT thereby lowering the amount of radiation transmitted through the patient or object.

Experimentally, dose reductions of 40% or more have been shown to be achievable through the use of this invention with transmission electron microscopy and in small animal x-ray MicroCT studies. This application of the invention is particularly useful in Fluoroscopic imaging and medical x-ray CT where a high radiation dose is imparted to the patient as the result of the imaging procedure. In the case of emission CT, it is possible to lower the amount of radioactive material that is given to a patient due to higher resolution and signal to noise ratio provided be the present invention.

Another important application of the present invention is in high speed imaging. In many tomographic imaging systems, the scan time depends on the number of projections and the flux of the transmission source. As previously described the number of projections and or the flux can be reduced due to the increased accuracy of the methods. Consequently, the scan time can be greatly reduced while achieving suitable images. This may prove to be very valuable in applications, such as imaging the heart or another moving organ, where scan time is often critical.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A method for reconstructing an image representation of an object from its projections, comprising:
obtaining projection data;
mapping Fourier transformed projection data in Fourier space;
converting iteratively said projection data from Fourier space to object space;
modifying said projection data in Fourier space and in object space to produce progressively modified projection data; and
generating an image from said modified projection data.

2. A method as recited in claim 1, further comprising:
processing said projection data to correct for at least variations in detection efficiency, attenuation, and scatter prior to Fourier transformation.

3. A method as recited in claim 1, further comprising:
solving for missing or incomplete projection data after mapping projections in Fourier space.

4. A method as recited in claim 1, further comprising:
padding said projection data with zeros.

5. A method as recited in claim 2, wherein said conversion of projection data between Fourier space and object space is performed by an inverse Fourier transform.

6. A method as recited in claim 5, wherein said inverse Fourier transform is an Inverse Pseudopolar Fast Fourier Transform.

7. A method as recited in claim 1, wherein said modification of the Fourier space data comprises replacing the Fourier space data at the locations corresponding to experimentally known projection data with the actual transformed experimental projections.

8. A method as recited in claim 1, wherein said initializing modification of Fourier space compromises assigning values to designated locations in Fourier space prior to inverse transformation.

9. A method as recited in claim 1, wherein said modification of the object space image to produce a modified object space image comprises:
   modifying the values of a designated set of pixels so the modified values are closer to the set of predefined values.

10. A method for reconstructing an image of an object from its projections, comprising:
   obtaining projection data;
   generating a Fourier transform of the projections at a plurality of angles and slice locations;
   placing the transformed projections onto a grid in Fourier space;
   performing an initializing modification of Fourier space;
   performing an inverse transformation of said Fourier space data to provide an object space image;
   modifying said object space image to produce a modified object space image;
   performing a forward Fourier transformation on said modified object space image to produce Fourier space data;
   modifying said Fourier space data to produce a modified Fourier space data; and
   applying said inverse Fourier transformation, modification, forward Fourier transformation and modification steps iteratively to the said modified Fourier space data until a termination condition is satisfied to provide a final image.

11. A method as recited in claim 10, further comprising:
   reformulating the obtained projection data into a parallel beam format prior to Fourier transform generation.

12. A method as recited in claim 11, wherein said reformulation of projection data comprises:
   mathematically transforming projections from a system geometry to a parallel beam geometry.

13. A method as recited in claim 11, wherein said reformulation of projection data comprises:
   applying a rebinning algorithm to transform system projection data into a parallel beam format.

14. A method as recited in claim 11, wherein said reformulation of projection data comprises:
   reconstructing obtained projection data with standard algorithms for fan/cone beams;
   performing a 2D Fourier transform across all projection slices;
   extracting 1D Fourier transformed projections from said 2D transforms in accordance to the Fourier Slice Theorem; and
   performing an inverse 1D Fourier transform of said 1D transform projections to provide parallel beam projection data.

15. A method as recited in claim 10, wherein said Fourier transform of the projections at a plurality of angles and slices comprises a Fractional Fourier Transform.

16. A method as recited in claim 15, wherein said Fractional Fourier Transform is set to match points and lines of the Fourier space grid.

17. A method as recited in claim 16, wherein said Fourier space grid is a pseudopolar grid.

18. A method as recited in claim 10, wherein said generating a Fourier transform of the projections at a plurality of angles and slice locations is performed by Non Uniform Fourier Transformation.

19. A method as recited in claim 10, wherein said generating a Fourier transform of the projections at a plurality of angles and slice locations is performed by a uniform Fourier transform.

20. A method as recited in claim 10, further comprising:
   padding said projections with zeros.

21. A method as recited in claim 10, wherein said placement of transformed projections onto a grid in Fourier space is performed by interpolating the location and values of a transformed projection onto the Fourier space grid.

22. A method as recited in claim 10, wherein said placement of transformed projections onto a grid in Fourier space is performed by a Gridding method.

23. A method as recited in claim 10, further comprising:
   reconstructing projections from a set of slices independently from of all other slices.

24. A method as recited in claim 10, wherein said initializing modification of Fourier space compromises assigning values to designated locations in Fourier space prior to inverse transformation.

25. A method as recited in claim 24, wherein said designated locations in Fourier space correspond to a full or partial set of the non-experimental regions.

26. A method as recited in claim 25, wherein said designated locations in Fourier space correspond to points beyond a resolution circle.

27. A method as recited in claim 25, wherein said values are determined from a transformation of a prior reconstruction of the projection data.

28. A method as recited in claim 10, wherein said initializing modification of Fourier space comprises:
   extending the Fourier space grid and padding said Fourier space data with zeros.

29. A method as recited in claim 10, wherein said Fourier space is on a pseudopolar grid and said inverse Fourier transform is an Inverse Pseudopolar Fast Fourier Transform algorithm.

30. A method as recited in claim 10, wherein said Fourier space is on a pseudopolar grid and said Fourier transform is a Pseudopolar Fast Fourier Transform algorithm.

31. A method as recited in claim 10, wherein said Fourier space is on a Cartesian grid and said inverse Fourier transform is a uniform inverse Fast Fourier Transform algorithm.

32. A method as recited in claim 10, wherein said Fourier space is on a pseudopolar grid and said Fourier transform is a non-uniform Fast Fourier Transform algorithm.

33. A method as recited in claim 10, wherein said modification of the Fourier space data comprises replacing the Fourier space data at the locations corresponding to experimentally known projection data with the actual transformed experimental projections.

34. A method as recited in claim 10, wherein said modification of the Fourier space data comprises replacing the Fourier space data at only a partial set of locations corresponding to experimentally known projection.

35. A method as recited in claim 34, wherein said replacing of Fourier space data is only performed at experimental locations where the Fourier data at the given location is substantially different, according to a certain defined criteria, from the value of the actual transformed experimental projection at that location.

36. A method as recited in claim 10, further comprising:
storing the locations and values of the Fourier space data corresponding to experimental regions; and
storing the locations and values of the Fourier space data corresponding to defined non-experimental regions.

37. A method as recited in claim 10, wherein said modification of the object space image to produce a modified object space image comprises:
designating a set of pixels for modification in accordance with predefined criteria.

38. A method as recited in claim 10, wherein said modification of the object space image to produce a modified object space image comprises:
modifying the values of a designated set of pixels so the modified values are closer to a set of predefined values.

39. A method as recited in claim 38, wherein said defined criteria for designating pixels modification comprises:
designating pixels only if the pixel values of the current iteration are different from a set of expected or physical values by more than a prescribed percentage.

40. A method as recited in claim 10, wherein said modification of the object space image to produce a modified object space image comprises:
finding pixels that have unphysical or unexpected values according to a set of predefined criteria; and
modifying the values of the pixels with unphysical values so that the modified values are potentially closer to the set of physical or expected values.

41. A method as recited in claim 40, wherein said modification comprises:
modifying the values of the said pixels by multiplying said values by a constant, subtracting from this corresponding pixel values from a previous iteration that have been multiplied by a potentially different constant and adding to this a set of physical or expected values that have been multiplied by a constant that is potentially different from all other constants.

42. A method as recited in claim 10, wherein said termination condition comprises a predetermined number of iterations of inverse Fourier transformation, modification, forward Fourier transformation and modification steps.

43. A method as recited in claim 10, wherein said termination condition comprises:
monitoring an image quality parameter; and
terminating at the occurrence of desired value of said image quality parameter.

44. A method as recited in claim 10, wherein said termination condition comprises:
monitoring an error function; and
terminating at the occurrence of a monitored error.

45. A method as recited in claim 10, wherein said termination condition comprises:
monitoring an error function; and
terminating if the error does not improve in a set number of iterations.

46. A method as recited in claim 10, wherein the final reconstructed image is based on the derived data from an iteration that is not the last iteration of the cycle.

47. A method as recited in claim 10, wherein the final reconstructed image is based upon the iteration with the best designated image quality parameter.

48. A method as recited in claim 45, wherein said error function is based upon comparison of the Fourier space data of current iteration at the locations corresponding to experimental regions to the actual transformed experimental projection data at the same locations.

49. A method for tomographic imaging, comprising:
obtaining equally sloped projection data from an imager;
padding projection data with zeros with a suitable amount of zeros;
generating a one dimensional Fractional Fast Fourier transform of the projections at a plurality of angles and slice locations;
placing the transformed projections onto a pseudopolar grid in Fourier space;
storing locations and values of said Fourier transformed projections;
performing a inverse two dimensional Pseudopolar Fast Fourier Transform of each 2D slice in Fourier space to provide object space data;
modifying said object space data to produce a modified object space data;
performing a forward two dimensional Pseudopolar Fast Fourier Transform of each 2D slice of object space data to produce Fourier space data;
modifying said Fourier space data to produce a modified Fourier space data; and
applying said inverse Fourier transformation, modification, forward Fourier transformation and modification steps iteratively to the said modified Fourier space data until a termination condition is satisfied to provide a final image.

50. A method as recited in claim 49, further comprising:
rotating or arranging the imaging subject, detectors, and or source of a tomographic imaging system in manner that the projection data, when reformulated, lie within experimental error along isocentric lines formed by grid points of said grid in Fourier space.

51. A method as recited in claim 50, wherein said grid in Fourier space is a set of 2D pseudopolar grids.

52. A method as recited in claim 50, wherein said grid in Fourier space is a 3D pseudopolar grid or a stacked set of 3D pseudopolar grid.

53. A method as recited in claim 50, wherein said grid in Fourier space is a polar grid.

54. A method as recited in claim 50, wherein said grid in Fourier space is a 3D polar grid or a stacked set of 3D polar grid.

55. A non-transitory computer-readable storage medium having an executable program stored thereon, wherein the program instructs a computer to perform steps comprising:
obtaining projection data;
mapping Fourier transformed projection data in Fourier space;
converting iteratively the projection data from Fourier space to object space;
modifying said projection data in Fourier space and in object space to produce progressively modified projection data; and
generating an image from said modified projection data.

* * * * *